(12) United States Patent
Root et al.

(10) Patent No.: US 8,532,760 B2
(45) Date of Patent: *Sep. 10, 2013

(54) METHOD AND APPARATUS FOR A SMALL POWER SOURCE FOR AN IMPLANTABLE DEVICE

(71) Applicant: Cardiac Pacemakers, Inc., St. Paul, MN (US)

(72) Inventors: Michael J. Root, Lino Lakes, MN (US); Nick A. Youker, River Falls, WI (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,860

(22) Filed: Nov. 12, 2012

(65) Prior Publication Data

US 2013/0073004 A1    Mar. 21, 2013

Related U.S. Application Data

(63) Continuation of application No. 12/966,444, filed on Dec. 13, 2010, now Pat. No. 8,311,627, which is a continuation of application No. 11/611,635, filed on Dec. 15, 2006, now Pat. No. 7,860,564.

(60) Provisional application No. 60/750,478, filed on Dec. 15, 2005, provisional application No. 60/750,718, filed on Dec. 15, 2005.

(51) Int. Cl.
*A61N 1/00* (2006.01)

(52) U.S. Cl.
USPC .......................................................... 607/2

(58) Field of Classification Search
USPC ...................................................... 607/2, 36
See application file for complete search history.

(56) References Cited

U.S. PATENT DOCUMENTS

| | | | |
|---|---|---|---|
| 3,970,478 | A | 7/1976 | Jurva |
| 4,122,241 | A | 10/1978 | Ciliberti, Jr. et al. |

(Continued)

FOREIGN PATENT DOCUMENTS

| | | | |
|---|---|---|---|
| JP | 2008-519402 A | 6/2008 | |
| JP | 2008519402 A | 6/2008 | |

(Continued)

OTHER PUBLICATIONS

"U.S. Appl. No. 11/611,635, Examiner Interview Summary mailed Aug. 18, 2010", 1 pg.

(Continued)

*Primary Examiner* — George Manuel
*Assistant Examiner* — Robert N Wieland
(74) *Attorney, Agent, or Firm* — Schwegman Lundberg & Woessner, P.A.

(57) ABSTRACT

One example includes a battery that includes a stack of at least one substantially planar anode and at least one substantially planar cathode, wherein the stack defines a contoured exterior, and a battery housing enclosing the stack, the battery housing defining a battery housing exterior, wherein the contoured exterior of the stack is shaped to conform to a contoured interior of the battery housing that approximately conforms to the battery housing exterior, the battery produced by the process of modeling, using fluid dynamics, an exterior of a biocompatible housing and shaping the battery housing to conform to at least some of the exterior of the biocompatible housing.

20 Claims, 7 Drawing Sheets

(56) References Cited

U.S. PATENT DOCUMENTS

| | | | |
|---|---|---|---|
| 4,333,469 | A | 6/1982 | Jeffcoat et al. |
| 5,497,140 | A | 3/1996 | Tuttle |
| 5,925,030 | A | 7/1999 | Gross et al. |
| 6,445,948 | B1 | 9/2002 | Somdahl et al. |
| 6,613,474 | B2 | 9/2003 | Frustaci et al. |
| 6,664,335 | B2 | 12/2003 | Krishnan |
| 6,730,136 | B2 | 5/2004 | Webber |
| 6,862,465 | B2 | 3/2005 | Shults et al. |
| 7,611,549 | B2 * | 11/2009 | Haasl .................... 29/623.5 |
| 7,860,564 | B2 | 12/2010 | Root et al. |
| 8,301,242 | B2 | 10/2012 | Root et al. |
| 2002/0090389 | A1 | 7/2002 | Humes et al. |
| 2003/0114735 | A1 | 6/2003 | Silver et al. |
| 2004/0091784 | A1 | 5/2004 | Frederiksson et al. |
| 2004/0127952 | A1 * | 7/2004 | O'Phelan et al. ............ 607/36 |
| 2004/0215243 | A1 | 10/2004 | Houben et al. |
| 2004/0215286 | A1 | 10/2004 | Stypulkowski |
| 2005/0021108 | A1 | 1/2005 | Klosterman et al. |
| 2005/0057905 | A1 | 3/2005 | He et al. |
| 2007/0092794 | A1 | 4/2007 | Coffey et al. |
| 2007/0099071 | A1 | 5/2007 | Morgan et al. |
| 2007/0179532 | A1 | 8/2007 | Root et al. |
| 2010/0304209 | A1 | 12/2010 | Lund et al. |
| 2010/0305628 | A1 | 12/2010 | Lund et al. |
| 2010/0305636 | A1 | 12/2010 | Lund et al. |
| 2011/0082509 | A1 | 4/2011 | Root et al. |
| 2012/0143271 | A1 | 6/2012 | Root et al. |

FOREIGN PATENT DOCUMENTS

| | | |
|---|---|---|
| WO | WO-2005014069 A1 | 2/2005 |
| WO | WO-2006050098 A1 | 5/2006 |
| WO | WO-2007070718 A2 | 6/2007 |
| WO | WO-2007070718 A3 | 6/2007 |

OTHER PUBLICATIONS

"U.S. Appl. No. 11/611,635, Non Final Office Action mailed Sep. 4, 2009", 9 pgs.

"U.S. Appl. No. 11/611,635, Non-Final Office Action mailed Mar. 25, 2010", 11 pgs.

"U.S. Appl. No. 11/611,635, Notice of Allowance mailed Aug. 18, 2010", 9 pgs.

"U.S. Appl. No. 11/611,635, Response filed Feb. 4, 2010 to Non-Final Office Action mailed Sep. 4, 2009", 9 pgs.

"U.S. Appl. No. 11/611,635, Response filed Jun. 24, 2010 to Non-Final Office Action mailed Mar. 25, 2010", 12 pgs.

"U.S. Appl. No. 12/966,444, Non Final Office Action mailed Mar. 12, 2012", 9 pgs.

"U.S. Appl. No. 12/966,444, Non-Final Office Action mailed May 23, 2011", 7 pgs.

"U.S. Appl. No. 12/966,444, Notice of Allowance mailed Jul. 5, 2012", 9 pgs.

"U.S. Appl. No. 12/966,444, Notice of Allowance mailed Oct. 11, 2011", 9 pgs.

"U.S. Appl. No. 12/966,444, Response filed May 22, 2012 to Non Final Office Action mailed Mar. 12, 2012", 7 pgs.

"U.S. Appl. No. 12/966,444, Response filed Aug. 17, 2011 to Non-Final Office Action mailed May 23, 2011", 9 pgs.

"U.S. Appl. No. 13/372,039, Non Final Office Action mailed Apr. 6, 2012", 10 pgs.

"U.S. Appl. No. 13/372,039, Notice of Allowance mailed Jun. 28, 2012", 12 pgs.

"U.S. Appl. No. 13/372,039, Response filed May 30, 2012 to Non Final Office Action mailed Apr. 6, 2012", 7 pgs.

"European Application Serial No. 10163825.2, Response filed Oct. 1, 2012 to Extended European Search Report mailed Mar. 7, 2012", 10 pgs.

"European Application Serial No. 06845670.6, Communication mailed Oct. 2, 2008", 2 pgs.

"European Application Serial No. 10163825.2, Extended Search Report mailed Mar. 7, 2012", 6 pgs.

"International Application Serial No. PCT/US2006/048127, International Search Report mailed Sep. 12, 2007", 6 pgs.

"International Application Serial No. PCT/US2006/048127, Written Opinion mailed Sep. 12, 2007", 6 pgs.

"Japanese Application Serial No. 2008-545880, Examiners Decision of Final Refusal mailed Sep. 18, 2012", (w/ English Translation), 4 pgs.

"Japanese Application Serial No. 2008-545880, Office Action dated Feb. 7, 2012", (w/ English Translation), 8 pgs.

"Japanese Application Serial No. 2008-545880, Response filed Jun. 6, 2012 to Office Action mailed Feb. 7, 2012", English Claims with Resposne, 11 pgs.

Marincic, N., et al., "Lithium inorganic battery for cardiac pacemaker application", Electrochemical Society Fall Meeting, Extended Abstract, (1975), 101-102.

* cited by examiner

METHOD AND APPARATUS FOR A SMALL POWER SOURCE FOR AN IMPLANTABLE DEVICE

CROSS-REFERENCE TO RELATED APPLICATIONS

This application is a Continuation of U.S. application Ser. No. 12/966,444, filed on December 13, now issued as U.S. Pat. No. 8,311,627, which is a Continuation of U.S. application Ser. No. 11/611,635, filed on Dec. 15, 2006, now issued as U.S. Pat. No. 7,860,564, the benefit of priority of each is claimed herein, and which are incorporated herein by reference in their entirety.

This application claims the benefit under 35 U.S.C. 119(e) of U.S. Provisional Patent Application Ser. No. 60/750,478, filed Dec. 15, 2005, the entire disclosure of which is hereby incorporated by reference in its entirety.

This application also claims the benefit under 35 U.S.C. 119(e) of U.S. Provisional Patent Application Ser. No. 60/750,718, filed Dec. 15, 2005, the entire disclosure of which is hereby incorporated by reference in its entirety.

The following commonly assigned U.S. patent applications are related and are all incorporated by reference in their entirety: "Batteries Including a Flat Plate Design," U.S. Patent Publication No. 2004/0127952, filed Feb. 7, 2003, now U.S. Pat. No. 7,479,349, "Batteries Including a Flat Plate Design," U.S. Provisional Application Ser. No. 60/437,537 filed Dec. 31, 2002; "System and Method for Sealing Battery Separator," Ser. No. 11/264,996, filed Nov. 2, 2005, now U.S. Patent Publication No. 2007/0099194; and "Method and Apparatus for Improved Battery Profile," U.S. Provisional Application Ser. No. 60/750,517, filed Dec. 15, 2005.

TECHNICAL FIELD

This disclosure relates generally to implantable medical devices, and more particularly to and implantable medical device having an improved profile.

BACKGROUND

Batteries are available to provide energy for self-powered devices. Various chemistries, construction methods, and battery profiles have been developed for use in self-powered devices. But as technology evolves, new applications would benefit from new battery configurations. For example, known applications could benefit from improvements in battery chemistries, constructions methods, and battery profiles. Specifically, improved battery profiles could enable improved device profiles, which could widen the range of possible implantation locations. Such a range would widen, in part, because improved shapes could address existing problems, such as non-preferred levels of hemodynamic drag, turbulence, fluid sheer stress and stagnation.

Certain implantable devices have been developed to operate in remote portions of the human body. These remote devices include, for example, remote sensors or neurostimulation devices. Depending on the implant location, remote devices must be small enough to fit into various confined areas of the human body. Therefore, the size of these remote devices is typically considerably smaller than common devices, like cardiac rhythm management devices. The limited size of remote devices correspondingly limits the size of the components of the devices, including its power source or battery.

Improved batteries should provide as much electrical performance as existing battery designs. Additionally, new designs should be compatible with efficient manufacturing methods. Further, new designs should offer a wide range of configurations to make possible various applications.

SUMMARY

The above-mentioned problems and others not expressly discussed herein are addressed by the present subject matter and will be understood by reading and studying this specification.

One embodiment of the present subject matter includes an electrochemical power source for use with a remote implantable medical device. The electrochemical power source includes a housing geometrically defined to reside with an implantable medical device. The power source also includes at least one anode, at least one cathode, and an electrolyte within the housing. The electrochemical power source has a displacement volume of below 0.024 cubic centimeters and is adapted to provide electrical current used to operate the device. According to one embodiment, the implantable medical device includes a remote implantable sensor. The implantable medical device includes a remote neurostimulation device, according to an embodiment. The electrochemical power source can be rechargeable in various embodiments. The power source includes a rechargeable power source, in one embodiment.

One aspect of this disclosure relates to an implantable medical device. The implantable medical device includes electronics adapted to provide designated medical functionality. The implantable medical device also includes at least one electrochemical power source adapted to provide electrical current to the device circuitry. The power source includes a housing geometrically defined to reside with the implantable medical device. The power source also includes at least one anode, at least one cathode, and an electrolyte within the housing. According to various embodiments, the power source has a displacement volume of below 0.024 cubic centimeters. The electronics includes sensor circuitry, stimulation circuitry, or a combination of sensor and stimulation circuitry, according to various embodiments.

One aspect of this disclosure relates to a method for manufacturing an electrochemical power source for use in an implantable medical device. According to various embodiments, the method includes providing a housing geometrically defined to reside with an implantable medical device. The method also includes providing at least one anode, at least one cathode, and an electrolyte within the housing. According to various embodiments, the power source has a displacement volume of below 0.024 cubic centimeters and is adapted to provide electrical current used to operate the device.

One embodiment of the present subject matter includes a battery disposed in an implantable device, the battery having a bobbin configuration.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to

DETAILED DESCRIPTION

Figure 1:
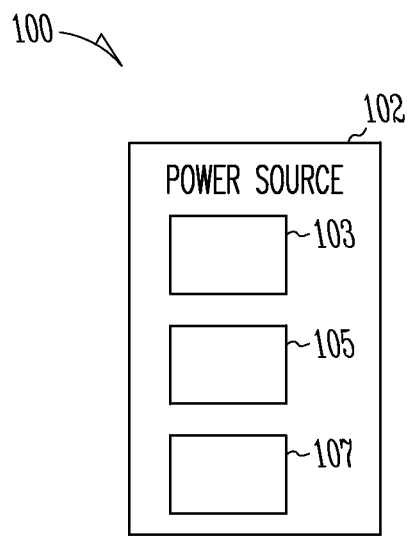
FIG. 1 illustrates a block diagram of an electrochemical power source for use in an implantable medical device, according to one embodiment.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Certain implantable devices have been developed to operate in remote portions of a patient. These remote devices include, for example, remote sensors, neurostimulation devices, and other devices. Depending on the implant location, remote devices must be small enough to fit into various confined areas of the human body. The requirements for such devices are unique compared to other applications because their size must be small enough to be noninvasive. Therefore, the size of these remote devices is typically considerably smaller than common devices, like cardiac rhythm management devices. The limited size of remote devices correspondingly limits the size of the components of the device, including its power source. While the power source is not as large, the power demands of these remote devices must still be satisfied.

Large batteries, with volumes on the order of 1 cubic centimeters or greater, are commonly used for devices such as cardiac pacemakers and defibrillators. Remote devices benefit from batteries which are a fraction of that size. Battery sizes smaller than 1 cubic centimeter are contemplated by the present subject matter.

The present subject matter extends to thin film batteries. Various thin film batteries are formed using vapor deposition of electrode and electrolyte materials onto a semiconductor substrate (such as silicon). However, achieving battery sizes small enough to meet the requirements of remote devices using thin film technology is problematic. Either very thick layers of deposition are required, or a number of thin film batteries must be stacked and connected in parallel. In either case, rendering the thin film battery or batteries into a cylindrical shape, which is often a requirement of remote device power sources, can be difficult. An improved power source for remote sensing and neurostimulation is needed.

This disclosure provides an efficient electrochemical power source for remote implantable medical devices. Battery chemistry and technology from large battery applications are adapted to appropriately size power sources for remote implantable medical devices, while ensuring that power and capacity demands of the devices are satisfied.

Electrochemical Power Source for Remote Applications

FIG. 1 illustrates a block diagram of an electrochemical power source for use in a remote implantable medical device, according to various embodiments. The electrochemical power source 100 includes a housing 102 geometrically defined to reside within a remote implantable medical device. The power source 100 includes at least one anode 103, at least one cathode 107, and an electrolyte 105 within the housing. In various embodiments, the electrochemical power source has a displacement volume of below 0.024 cubic centimeters and is adapted to provide electrical current used to operate the device. According to some embodiments, the remote implantable medical device includes a remote implantable sensor. The remote implantable medical device includes a remote neurostimulation device, according to some embodiments. The electrochemical power source is rechargeable in some embodiments.

Some examples of methodologies for device battery layouts are provided in U.S. patent application Ser. No. 11/264,966, filed on Nov. 2, 2005, entitled "System and method for sealing battery separator", which is commonly assigned and herein incorporated by reference in its entirety. According to various embodiments, the power source has a cylindrical shape. Non-cylindrical shapes (or form factors) additionally are covered by the present subject matter.

In some embodiments, the remote implantable medical device sized for placement in a blood vessel. In some of these embodiments, measurements are taken so that flow at the implant site can be modeled. Some embodiments use statistical models of the human body to model flow at the implant site. In various embodiments, the power source is sized to enable an implantable device which is shaped to provide the following benefits: reduced hydrodynamic drag, reduced turbulence, reduced stagnation and/or reduced fluid sheer stress. In various embodiments, the power source is small to enable such benefits. In some embodiments, the power source is shaped to conform to an interior of a device shaped to provide such benefits.

Various embodiments of the present subject matter include implantable medical devices. In various embodiments, implantable sensors are discussed. Implantable sensors, in various embodiments, are self-powered measurement devices. In some embodiments, these devices provide a wireless signal to one or more receivers. Receivers may be located in vivo or ex vivo. A transceiver relationship is additionally possible, in various embodiments.

Because of their implanted nature, implantable sensors should be as compact as possible. Device profile should be optimized for a minimally invasive implantation. As some embodiments are intended for endovascular use, several design parameters are important. For example, it is important to provide an implantable device which reduces hydrodynamic drag, turbulence, fluid sheer stress, and/or stagnation. An improper design in light of these phenomena can lead to the creation of an embolus, and can lead to occlusion of the vessel caused, in part, by the implanted device.

The present subject matter provides an implantable medical device, in various embodiments, which features an improved profile for implanted use. In some embodiments, the profile provides improved performance for endovascular use.

Figure 2:
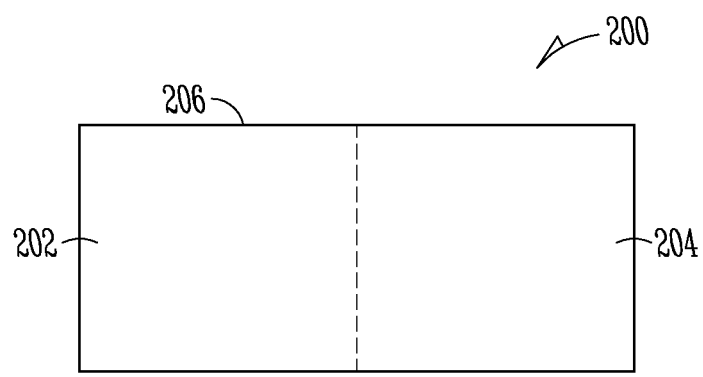
FIG. 2 shows a schematic of an implantable medical device, according to one embodiment of the present subject matter.

FIG. 2 shows a schematic of an implantable medical device 200, according to one embodiment of the present subject matter. Various embodiments of the present subject matter include electronics 204. Additionally, in various embodiments, a power source 202 is included. The implantable device 200 can be symmetrical along three, two, or no axes, in various embodiments. In various embodiments, the device includes a device shell 206. In some of these embodiments, the device shell 206 is hermetically sealed. In some embodiments, the device shell 206 is partially defined by a case which houses electrodes for the power source 202. A power source 202, in various embodiments, includes a battery. In additional embodiments, the power source 202 includes a capacitor.

Electronics 204, in various embodiments, include various components. Some embodiments include components adapted to communicate energy with devices external to the implantable medical device 200. In some of these embodiments, the energy is communicated wirelessly. Embodiments within the present subject matter include, but are not limited to, ultrasonic transducers, inductive transducers, and other wireless transducers.

Additional components are included as well. Electronics 204 include, in various embodiments, components for wireless communication of information to devices external to the implantable medical device. Additionally, in various embodiments, electronics 204 include sensor electronics which communicate data. Some of these embodiments include a pressure transducer. Also, in some embodiments, electronics 204 include stimulation electronics. Some of these embodiments include neurostimulation electronics. Some embodiments include a processor interconnected to other components to assist other components in communicating with each other. These components are not an exhaustive or exclusive list covering the scope of the present subject matter, and additional components not expressly listed herein additionally fall within the present scope.

In various embodiments, the device shell includes a profile which improves fluid flow. In some embodiments, the shell profile reduces hydrodynamic drag, turbulence, fluid sheer stress, and/or stagnation. In some embodiments, the shell is elongate. Some of these embodiments include a shell which is elongate, and which includes portions which have a circular cross section. An elongate shell is useful for implantation in a blood vessel in a manner which reduces hydrodynamic drag, turbulence, fluid sheer stress, and/or stagnation. Various embodiments include applications which have a profile adapted for implantation in a vein or in an artery. Various embodiments use an elongate shell in which the power source 202 and electronics 204 are stacked in a column along the interior of the elongate shell. In additional embodiments, the power source 202 and the electronics 204 are disposed side-by-side along the length of the elongate shell.

In various embodiments, hydrodynamic drag, turbulence, fluid sheer stress, and/or stagnation are determined using computational fluid dynamics. In some embodiments, measurements are taken of a target implant site. In some of these embodiments, the measurements are used to determine the shape of an implantable medical device which reduces hydrodynamic drag, turbulence, fluid sheer stress, and/or stagnation.

Some embodiments do not base modeling for reduced hydrodynamic drag, turbulence, fluid sheer stress, and/or stagnation on the measurement of an individual implant site. In some embodiments, the shape of the shell is determined based on reduced hydrodynamic drag, turbulence, fluid sheer stress, and/or stagnation in a statistically significant hypothetical model. For example, in some embodiments, a patient population is measured, and a model having blood-flow characteristics which typify the population is created. This model is used in the creation of a shell which reduces hydrodynamic drag, turbulence, fluid sheer stress, and/or stagnation, in various embodiments.

In some of these embodiments, a power source 202 is created to fill a portion of the interior of the implantable medical device in a manner which limits the amount of unused space. In some of these embodiments, the power source 202 is made from a stack of substantially planar power source 202 electrodes. Some embodiments use a stack of substantially planar power source 202 electrodes having different layers perimeters. Such a stack can have contours which are adapted to efficiently adhere to all or a portion of the interior space of the implantable medical device. Additional embodiments can use wound electrodes.

Battery embodiments having shapes which are determined as a function of improved fluid flow also fall within the scope of the present scope, including, but not limited to, battery embodiments having a prismatic shape, a generally cylindrical shape, and other shapes fall within the present scope.

In various embodiments, the implantable medical device 200 is adapted for reduced invasion during surgery. For example, in some embodiments, a profiles is used which delivers reduced tissue damage. Various embodiments include a profile having reduced tissue damage includes an elongate device having a length of from about 5 millimeters to about 10 millimeters. Devices up to 5 millimeters are possible, in various embodiments. Additional embodiments use devices of over ten millimeters. Additionally, various embodiments includes a profile which an average width of from about 1 millimeter to about 3 millimeters. Some embodiments are sized up to 1 millimeter. Additional embodiments are sized over 3 millimeters. Various embodiments are cylindrical, and are from about 5 to 10 millimeters long, and about 1 to 3 millimeters in diameter. Some embodiments are around 2.5 millimeters in diameter. Some embodiments are greater than 3 millimeters in diameter. Additionally, some embodiments are longer than 10 millimeters.

In some embodiments, the implantable medical device is elongate, with a proximal portion and a distal portion. In various embodiments, during implantation, the device is grasped at the proximal portion, and the distal portion is led through vasculature. In some of these embodiments, the distal portion has one or more edges. Edges, in various embodiments, are rounded to reduce tissue damage during implantation. Profiles which reduce tissue damage may also be included. For example, implantable medical devices having a parabolic distal portion fall within the present scope. Some of these embodiments are bullet shaped. Other profiles not expressly listed herein are additionally encompassed by the present scope.

In one process of the present subject matter, a profile of the implantable medical device 200 is determined as a function of power and size requirements. Power requirements, in various embodiments, are determined by the number of energy use events which occur during implantation. In some embodiments around 33 milliamp-hours are consumed per month, for example. It is understood that other devices using other power and size requirements are contemplated to be within the scope of this invention.

In some of these embodiments, power requirements are further defined by battery efficiency. Battery efficiency, in various embodiments, is a function of self-leakage. Power requirements are further determined by battery type. For example, some embodiments use primary batteries. Some embodiments use secondary batteries. Secondary batteries enable recharging. Recharging, in various embodiments, is depending on patient compliance. Recharging frequency should be reduced to increase patient satisfaction.

In an additional process of the present subject matter, a power requirement is determined and a power source 202 profile is selected to satisfy the power requirement and to satisfy a size requirement which reduces invasiveness. In some of these embodiments, a power management algorithm is developed to comply with these constraints. In some of these embodiments, a secondary power source 202 is used. In some of these embodiments, a power source 202 charging algorithm is used to improve power source 202 profile and the reduce requirements to a patient to visit a clinic to recharge the power source 202. In various embodiments, an iterative process of selecting a profile, and selecting a power management algorithm is used to determine the final profile of power source 202 which meets predetermined therapeutic requirements.

Various embodiments incorporate battery chemistries compatible with the present configurations. Embodiments within the present scope include, but are not limited to, at least one of a metal oxide, a metal sulfide, a metal selenide, a metal halide, a metal oxyhalide compound, and corresponding lithiated forms. Some of these embodiments include at least one of manganese, vanadium, silver, molybdenum, tungsten, cobalt, nickel, chromium, and main group compounds such as carbon monofluoride and iodine. Additionally, some embodiments include at least one of carbon, lithium, sodium, potassium, rubidium, cesium, magnesium, calcium, strontium, barium, tin, zinc or silver.

Primary battery chemistry embodiments fall within the present scope. Additionally, secondary battery chemistry embodiments fall within the present scope. In some embodiments a power source of an implantable medical device includes a plurality of batteries connected in series, parallel or a combination of series and parallel.

Various electrode constructions fall within the present scope. Embodiments compatible with the present subject matter include monolithic electrodes, pelleted electrodes, and other electrodes which have a solid shape. Pelleted electrodes, in various embodiments, include pellets formed from compressed powder, dough or slurry. Some electrode embodiments are formed from a tightly wound ribbon which is wound unto itself without an insulator to separate progressive wraps from one another. Additionally, some embodiment include an electrode onto which is pressed or coated an electronically conductive material. Other electrode configuration embodiments compatible with the present subject matter additionally fall within the present scope.

Additionally, various battery profiles using these electrodes fall within the present scope. Embodiments with the present scope include, but are not limited to, batteries having a cylindrical shape, batteries having a prismatic shape, batteries having a button shape, and batteries having other shapes. In some examples, batteries have shape which is determined as a function of the shape's impact on reducing blood flow. In some examples, batteries have shape which is determined as a function of the shape's impact on reducing tissue damage during implantation.

Figure 3:
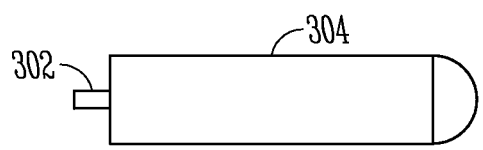
FIG. 3 shows a side view of an implantable medical device having a semi-spherical shaped portion, according to one embodiment of the present subject matter.

FIG. 3 shows a side view of an implantable medical device having a semi-spherical shaped portion, according to one embodiment of the present subject matter. In various embodiments, a protrusion 302 extends from the main portion 304 of the implantable device. The protrusion 302 is useful, in various embodiments, for positioning the device in a target implant site. For example, in some embodiments, a positioning lead grasps the device at protrusion 302. Protrusion 302 includes a texture, in various embodiments. For example, some embodiments of protrusion 302 include knurling. In various embodiments, the positioning lead positions the device while connected to the implantable device at the protrusion 302. In various embodiments, the positioning lead releases the implantable medical device. In various embodiments, the protrusion 302 provides a handle which is compatible with a clasp of a positioning lead, but in some embodiments, a protrusion is not included, and a positioning lead grasps the main body of the implantable medical device.

Figure 4:
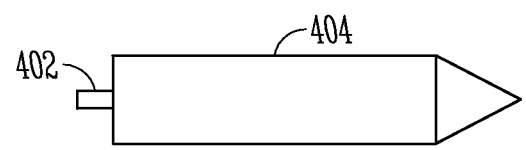
FIG. 4 shows a side view of an implantable medical device having a polyhedral portion, according to one embodiment of the present subject matter.

FIG. 4 shows a side view of an implantable medical device having a polyhedral portion, according to one embodiment of the present subject matter. The implantable medical device pictured includes a protrusion 402, and a main portion 404. The main portion 404 is shaped like a polyhedron, in some embodiments. In additional embodiments, it is cone shaped.

Figure 5:
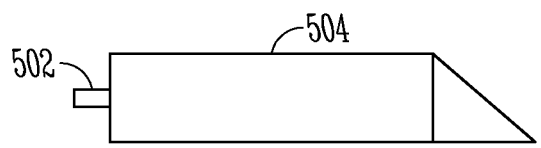
FIG. 5 shows a side view of an implantable medical device having a polyhedral portion, according to one embodiment of the present subject matter.

FIG. 5 shows a side view of an implantable medical device having a polyhedral portion, according to one embodiment of the present subject matter. The implantable medical device pictured includes a protrusion 502, and a main portion 504. The pictured embodiment has a chisel shape.

Figure 6:
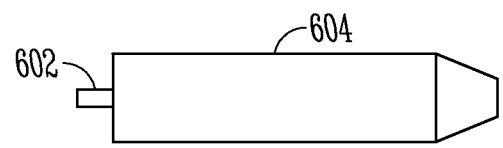
FIG. 6 shows a side view of an implantable medical device, according to one embodiment of the present subject matter.

FIG. 6 shows a side view of an implantable medical device, according to one embodiment of the present subject matter. The implantable medical device pictured includes a protrusion 602, and a main portion 604. In various embodiments, the implantable medical device has a distal portion which is shaped like a cone with the tip missing. In additional embodiments, the main portion 604 is a polyhedron. In some embodiments, the main portion 604 is bullet shaped.

The shapes described and pictured herein do not define an exhaustive or an exclusive list of the possible shapes within the present subject matter. Additional shapes fall within the present scope. For example, additional shapes which reduce hydrodynamic drag, turbulence, fluid sheer stress, and/or stagnation, fall within the present scope.

In various embodiments, an implantable medical device includes an improved shape enabled by the use of a battery which includes stacked electrodes. In some of these embodiments, the contour of the stack is non-linear, enabling the stack to occupy space within an implantable medical device efficiently. Additionally, in some embodiments, the battery is a coil.

Figure 7:
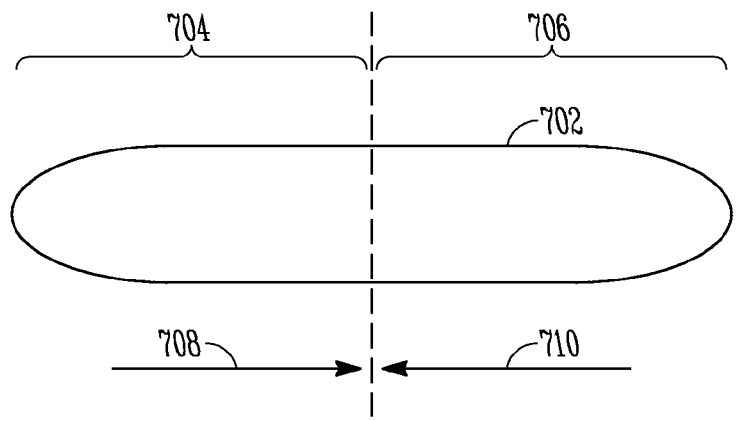
FIG. 7 shows a side view of an implantable medical device, according to one embodiment of the present subject matter.

FIG. 7 shows a side view of an implantable medical device, according to one embodiment of the present subject matter. The device 702 includes a first portion 704 which has a first profile shaped as a function of hydrodynamic drag, turbulence, fluid sheer stress, and/or stagnation. The device additionally includes a second portion 706 which has a second profile shaped as a function of hydrodynamic drag, turbulence, fluid sheer stress, and stagnation.

Blood flow is known to be bidirectional in a blood vessel. Additionally, as the heart pumps blood, the rate of blood flow of blood varies across a cross section of a blood vessel. Therefore, improved medical device embodiments are designed to offer increased performance in reducing hydrodynamic drag, turbulence, fluid sheer stress, and/or stagnation. The present subject matter includes a device having a first portion 704 which is shaped to offer improved compatibility with blood flow direction 708, in various embodiments. In some of these embodiments, the present subject matter includes a second portion 706 which is shaped to offer improved compatibility with blood flow direction 710. Blood flow direction 708 is approximately collinear with blood flow direction 710, in various embodiments.

Figure 8:
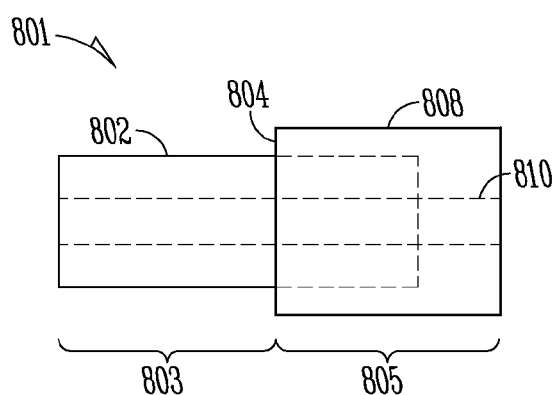
FIG. 8 shows a side view of an implantable medical device, according to one embodiment of the present subject matter.

FIG. 8 shows a side view of an implantable medical device, according to one embodiment of the present subject matter. In various embodiments, the device includes a first shell portion 803. In additional embodiments, a second shell portion 805 is attached to the first shell portion 803. The first shell portion 803 and the second shell portion 805 are hermetically sealed to one another with a hermetic seal 804, in various embodiments. Hermetic seals include welds, resins, and additional types of known hermetic seals.

In various embodiments, the first shell portion 802 doubles as a case for a battery. For example, in some embodiments, a battery anode and cathode are disposed in a case 802. Battery case embodiments include a drawn case portion mated to another case portion, in some examples. In some of these examples, a drawn case portion is sealed to another case portion with a battery case seal. In embodiments where the implantable medical device 801 requires a hermetically sealed exterior, and the battery case seal is exposed to the environment of the implantable medical device, the battery case seal is hermetic. In embodiments where the battery case seal is not exposed to the environment, the battery case seal may not be hermetic. For example, in some non-hermetic embodiments, the battery case seal is adapted to resist the flow of battery electrolyte.

The implantable medical device 801, in various embodiments, includes an optional cavity 810. In various embodiments, the cavity passes through the implantable medical device 801. In additional embodiments, the cavity does not pass through the implantable medical device 801, but instead defines an interior cavity.

An optional cavity 810, in various embodiments, is defined by a cylindrical opening which is concentric to an overall cylindrical shape of the implantable medical device 801, in some embodiments. Some configurations of the present subject matter are toroidally shaped. Some shapes of the present subject matter resemble an extruded toroid. In various embodiments, the cavity is irregular.

Figure 9:
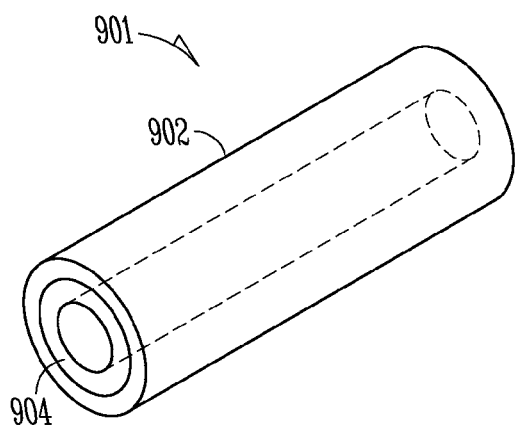
FIG. 9 shows a perspective view of an implantable medical device, according to one embodiment of the present subject matter.

FIG. 9 shows a perspective view of an implantable medical device, according to one embodiment of the present subject matter. In various embodiments, an implantable medical device 901 includes a first portion 904 and a second portion 902. In some embodiments, the second portion 902 includes electronics. Some of these embodiments include pressure transducers. In additional embodiments, the second portion 902 includes a battery. In some of the embodiments, the battery is housed in the case which is the same as the exterior of the second portion 902.

In some embodiments, the first portion 904 includes electronics. Some of these embodiments include pressure transducers. In additional embodiments, the first portion 904 includes a battery. In some of the embodiments, the battery is housed in the case which is the same as the exterior of the first portion 904.

In some embodiments, the first portion 904 extends through the second portion 902. In some of these embodiments, a cavity extends through the first portion 904. A cavity assists in improving performance with respect to hydrodynamic drag at the implant site, turbulence at the implant site, fluid sheer stress at the implant site, and/or stagnation at the implant site. For example, in some embodiments, a cavity discourages emboli formation.

Returning to FIG. 1, according to various embodiments, an outer surface of the housing is coated with a biocompatible coating. Some of these embodiments include drug eluting coatings. Some of these coatings reduce various unwanted effects, such as stenosis. Additionally, some eluting coatings deliver chemical therapy. Examples of biocompatible coatings are provided in U.S. Pat. No. 6,664,335, entitled "Polyurethane elastomer article with 'shape memory' and medical devices therefrom", which is commonly assigned and incorporated herein by reference in its entirety. Other types of coatings are contemplated by the present subject matter.

Various cathode configurations are contemplated by the present subject matter. The physical forms of cathode 107 used in various embodiments include, but are not limited it, compressed powder, dough and/or slurry. In various embodiments, the cathode can be formed by the processes including, but not limited to, disposing the cathode directly in the battery container, pressing the cathode into the battery container, and/or pressing the cathode onto an electrically conductive material. Cathodes compositions contemplated by the present subject matter include, but are not limited to, one or more of the following: metal oxide, metal sulphide, metal selenide, metal halide, metal oxyhalide compound and/or their corresponding lithiated forms. The cathode may include manganese, vanadium, silver, molybdenum, tungsten, cobalt, nickel, or chromium. The cathode may also include a main group compound such as carbon monofluoride or iodine. Other compositions of the cathode are within the scope of this disclosure.

Anodes of the present subject matter include, but are not limited to, carbon and/or metals. Anode compositions include, but are not limited to, one or more of the following: metals such as lithium, sodium, potassium, rubidium, cesium, magnesium, calcium, strontium, barium, tin, zinc and/ or silver, and other anode compositions not expressly recited herein.

The electrochemical power source 100 is capable of supporting charging and discharging currents on the order of 10 mA to 1 pA, according to various embodiments. Waveforms contemplated by the present subject matter include, but are not limited to, continuous, pulsed and other waveforms. Additional levels of charging and discharging currents can be supported using the disclosed power source without departing from the scope of the disclosure. Various electrochemical power sources of the present subject matter are designed and the components and chemistries selected to ensure a reduced level of self-discharge. Some embodiments are constructed to encourage detectable State of Charge or Depth of Discharge (DoD) indicated when monitoring open-circuit cell voltage (OCV). Various power sources of the present subject matter are designed to have a near-linear OCV vs. DOD curve for the first 60-90% of DoD.

Remote Implantable Medical Devices

Figure 10:
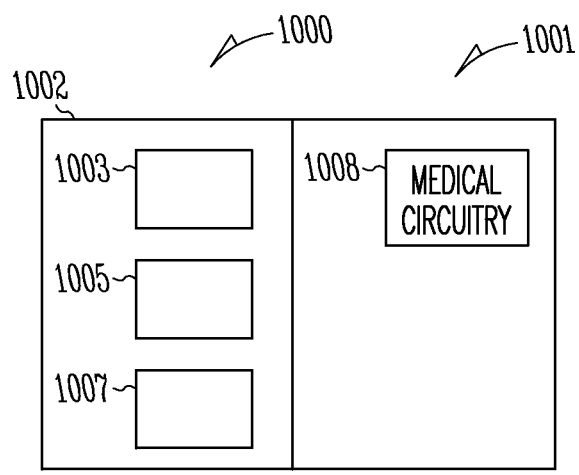
FIG. 10 illustrates a block diagram of a remote implantable medical device, according to one embodiment.

FIG. 10 illustrates a block diagram of an implantable medical device, according to one embodiment. The implantable medical device 1001 includes electronics 1008. The implantable medical device 1001 also includes at least one electrochemical power source 1000 adapted to provide electrical current to the electronics. A power source 1000, in various embodiments, includes a battery. In additional embodiments, the power source 1000 includes a capacitor. The power source 1000 includes a housing 1002 geometrically defined to reside with the remote implantable medical device. The power source also includes at least one anode 1003, at least one cathode 1007, and an electrolyte 1005 within the housing. According to various embodiments, the power source has a displacement volume of below 0.024 cubic centimeters. According to various embodiments, the at least one power source includes multiple power sources electrically connected in series, connected in parallel, or connected in a combination of series and parallel, to provide the necessary electrical current to power the remote implantable medical device.

The electronics 1008 includes sensor circuitry, stimulation circuitry, and combinations thereof, according to various embodiments of the present subject matter. According to various embodiments, the electronics 1008 includes sensor circuitry adapted to provide diagnostic functions. Some of these embodiments include a pressure transducer. Embodiments within the present subject matter additionally include, but are not limited to, ultrasonic transducers, inductive transducers, and/or other transducers. The electronics 1008 may also include stimulation circuitry adapted to provide a therapeutic function, such as neurostimulation circuitry adapted to provide neurostimulation therapy.

Electronics 1008, in various embodiments, include various components. Some embodiments include components adapted to communicate other devices. In some embodiments, communications are conducted wirelessly. Communications with devices external to the implantable medical device 1001 are contemplated by the present subject matter. Additionally, wireless communications with receivers located in vivo are contemplated. Some embodiments include a processor interconnected to other components to assist components in communicating with each other. This list of components is not an exhaustive or exclusive list covering the present subject matter, and additional components not expressly listed herein additionally are contemplated.

The implantable device 1001 can be symmetrical along three, two, or no axes, in various embodiments. In various embodiments, the device includes a device housing 1002. In some of these embodiments, the device housing 1002 is hermetically sealed. In some embodiments, the device housing 1002 is partially defined by a case which houses electrodes for the power source 1000.

Embodiments of the present subject matter include a housing which has a shape which is modeled to achieve a fluid flow objective, in various embodiments. In some of these embodiments, a power source has a shape which is compatible with said device housing shape. In various embodiments, the device housing includes a profile which improves fluid flow. In some embodiments, the housing profile reduces hydrodynamic drag, turbulence, fluid sheer stress, and/or stagnation. In some embodiments, the housing is elongate. Some of these embodiments include a housing which is elongate, and which includes portions which have a circular cross section. An elongate housing is useful for implantation in a blood vessel in a manner which reduces hydrodynamic drag, turbulence, fluid sheer stress, and/or stagnation. Various embodiments include applications which have a profile adapted for implantation in a vein or in an artery. Various embodiments use an elongate housing in which the power source 1000 and electronics 1008 are stacked in a column along the interior of the elongate housing.

In various embodiments, hydrodynamic drag, turbulence, fluid sheer stress, and/or stagnation are determined using computational fluid dynamics. In some embodiments, measurements are taken of a target implant site. In some of these embodiments, the measurements are used to determine the shape of an implantable medical device which reduces hydrodynamic drag, turbulence, fluid sheer stress, and/or stagnation.

Some embodiments do not base modeling for reduced hydrodynamic drag, turbulence, fluid sheer stress, and/or stagnation on the measurement of an individual implant site. In some embodiments, the shape of the housing is determined based on reduced hydrodynamic drag, turbulence, fluid sheer stress, and/or stagnation in a statistically significant hypothetical model. For example, in some embodiments, a patient population is measured, and a model having blood-flow characteristics which typify the population is created. This model is used in the creation of a housing which reduces hydrodynamic drag, turbulence, fluid sheer stress, and/or stagnation, in various embodiments.

In some of these embodiments, a power source 1000 is created to fill a portion of the interior of the implantable medical device in a manner which limits the amount of unused space. In some of these embodiments, the power source 1000 is made from a stack of substantially planar power source 1000 electrodes. Some embodiments use a stack of substantially planar power source 1000 electrodes having different layers perimeters. Such a stack can have contours which are adapted to efficiently adhere to all or a portion of the interior space of the implantable medical device. Additional embodiments use wound electrodes.

Battery embodiments having shapes which are determined as a function of improved fluid flow also fall within the scope of the present scope, including, but not limited to, battery embodiments having a prismatic shape, a generally cylindrical shape, and other shapes fall within the present scope.

In various embodiments, the implantable medical device 201 is adapted for reduced invasion during surgery. For example, in some embodiments, a profile is used which delivers reduced tissue damage. Various embodiments include a profile having reduced tissue damage includes an elongate device having a length of from about 5 millimeters to about 10 millimeters. Devices up to 5 millimeters are possible, in various embodiments. Additional embodiments use devices of over 10 millimeters. Additionally, various embodiments include a profile which has an average width of from about 1 millimeter to about 3 millimeters. Some embodiments are sized up to 1 millimeter. Additional embodiments are sized over 3 millimeters. Various embodiments are cylindrical, and are from about 5 to 10 millimeters long, and about 1 to 3 millimeters in diameter. Some embodiments are around 2.5 millimeters in diameter. Some embodiments are greater than 3 millimeters in diameter. Additionally, some embodiments are longer than 10 millimeters.

In some embodiments, the implantable medical device is elongate, with a proximal portion and a distal portion. In various embodiments, during implantation, the device is grasped at the proximal portion, and the distal portion is led through vasculature. In some of these embodiments, the distal portion has one or more edges. Edges, in various embodiments, are rounded to reduce tissue damage during implantation. Profiles which reduce tissue damage may also be included. For example, implantable medical devices having a parabolic distal portion fall within the present scope. Some of these embodiments are bullet shaped. Other profiles not expressly listed herein are additionally encompassed by the present scope.

In one process of the present subject matter, a profile of the implantable medical device 1001 is determined as a function of power and size requirements. Power requirements, in various embodiments, are determined by the number of energy use events which occur during implantation. In some embodiments around 33 milliamp-hours are consumed per month, for example. It is understood that other devices using other power and size requirements are contemplated to be within the scope of this invention.

In some embodiments, power requirements are further defined by battery efficiency. Battery efficiency, in various embodiments, is a function of self-leakage. Power requirements are further determined by battery type. For example, some embodiments use primary batteries. Some embodiments use secondary batteries. Secondary batteries enable recharging. Recharging, in various embodiments, is depending on patient compliance. Recharging frequency should be reduced to increase patient satisfaction.

In an additional process of the present subject matter, a power requirement is determined and a power source 1000 profile is selected to satisfy the power requirement and to satisfy a size requirement which reduces invasiveness. In some of these embodiments, a power management algorithm is developed to comply with these constraints. In some of these embodiments, a secondary power source 1000 is used. In some of these embodiments, a power source 1000 charging algorithm is used to improve power source 1000 profile and the reduce requirements to a patient to visit a clinic to recharge the power source 1000. In various embodiments, an iterative process of selecting a profile, and selecting a power management algorithm is used to determine the final profile of power source 1000 which meets predetermined therapeutic requirements.

Figure 11:
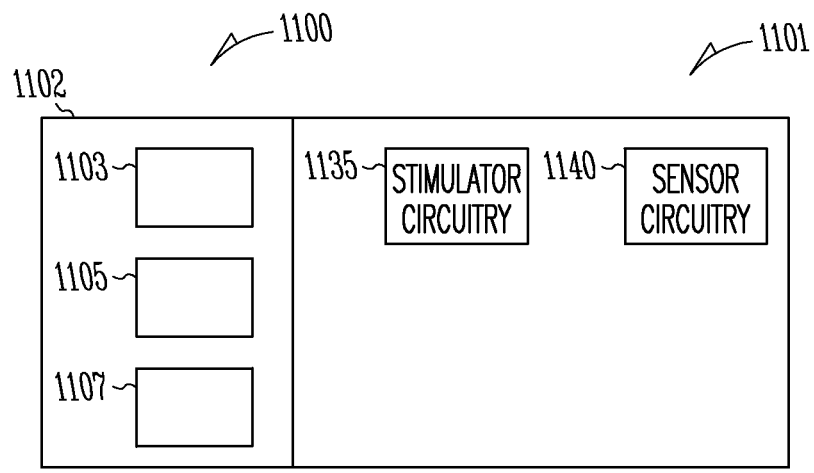
FIG. 11 illustrates a block diagram of a remote implantable medical device having sensing and stimulating capabilities, according to one embodiment.

FIG. 11 illustrates a block diagram of an implantable medical device having sensing and stimulating capabilities, according to one embodiment. The implantable medical device 1101 includes sensor circuitry 1140 adapted to provide a diagnostic function, such as sensing pressure, blood flow, or other measurable medical parameter. The implantable medical device 1101 also includes stimulator circuitry 1135 adapted to provide a therapeutic function. An example of stimulator circuitry 1135 includes neurostimulation circuitry adapted to provide neurostimulation therapy, while other types of stimulator circuitry are within the scope of this disclosure. The implantable medical device 1101 further includes at least one electrochemical power source 1100 adapted to provide electrical current to the stimulator and sensor circuitry. The power source 1100 includes a housing 1102 geometrically defined to reside with the remote implantable medical device. The power source also includes at least one anode 1103, at least one cathode 1107, and an electrolyte 1105 within the housing. According to various embodiments, the power source has a displacement volume of below 0.024 cubic centimeters.

Figure 12:
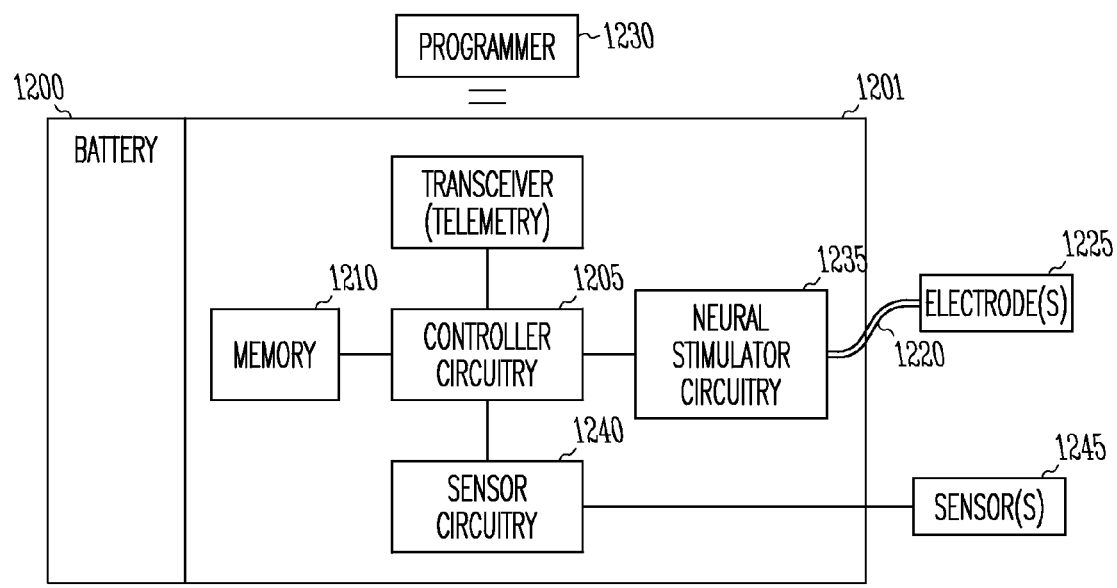
FIG. 12 illustrates a block diagram of a system with a remote implantable medical device having an electrochemical power source such as illustrated in FIG. 1, according to one embodiment.

FIG. 12 illustrates a block diagram of a system with a device having an electrochemical power source such as illustrated in FIG. 1, according to one embodiment. The system includes a device 1201, an electrical lead 1220 coupled to the device 1201, and at least one electrode 1225. The device includes a controller circuit 1205, a memory circuit 1210, a telemetry circuit 1215, and a neural stimulation circuit 1235. The device also includes a battery 1200 having a housing geometrically defined to reside with a remote implantable medical device. The battery 1200 also includes at least one anode, at least one cathode, and an electrolyte within the housing. The battery 1200 has a displacement volume of below 0.024 cubic centimeters. The battery is adapted to provide sufficient electrical power to operate the device. The battery may be rechargeable, according to an embodiment.

The controller circuit 1205 is operable on instructions stored in the memory circuit to deliver an electrical neural stimulation therapy. Therapy is delivered by the neural stimulation circuit 1235 through the lead 1220 and the electrode(s) 1225. The telemetry circuit 1215 allows communication with an external programmer 1230. The programmer 1230 can be used to adjust the programmed therapy provided by the device 1201, and the device can report device data (such as battery and lead resistance) and therapy data (such as sense and stimulation data) to the programmer using radio telemetry, for example. According to various embodiments, the device 1201 senses one or more physiological parameters and delivers neural stimulation therapy. The illustrated system also includes sensor circuitry 1240 that is coupled to at least one sensor 1245. The controller circuit 1205 processes sensor data from the sensor circuitry and delivers a therapy responsive to the sensor data.

Figure 13:
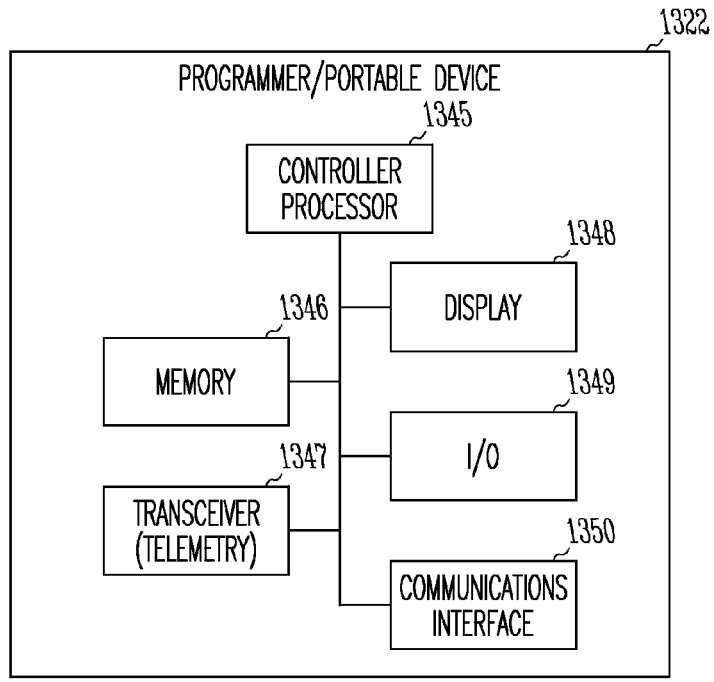
FIG. 13 illustrates a block diagram of a programmer such as illustrated in the system of FIG. 4 or other external device to communicate with the remote implantable medical device(s), according to one embodiment.

FIG. 13 illustrates a block diagram of a programmer such as illustrated in the system of FIG. 4 or other external device to communicate with the device(s), according to one embodiment. An example of another external device includes Personal Digital Assistants (PDAs) or personal laptop and desktop computers in a wireless patient monitoring network. The illustrated device 1322 includes controller circuitry 1345 and a memory 1346. The controller circuitry 1345 is capable of being implemented using hardware, software, and combinations of hardware and software. For example, according to various embodiments, the controller circuitry 1345 includes a processor to perform instructions embedded in the memory 1346 to perform a number of functions, including communicating data and/or programming instructions to the implantable devices. The illustrated device 1322 further includes a transceiver 1347 and associated circuitry for use to communicate with an implantable device. Various embodiments have wireless communication capabilities. For example, various embodiments of the transceiver 1347 and associated circuitry include a telemetry coil for use to wirelessly communicate with an implantable device. The illustrated device 1322 further includes a display 1348, input/output (I/O) devices 1349 such as a keyboard or mouse/pointer, and a communications interface 1350 for use to communicate with other devices, such as over a communication network.

Method for Manufacturing an Electrochemical Power Source

Figure 14:
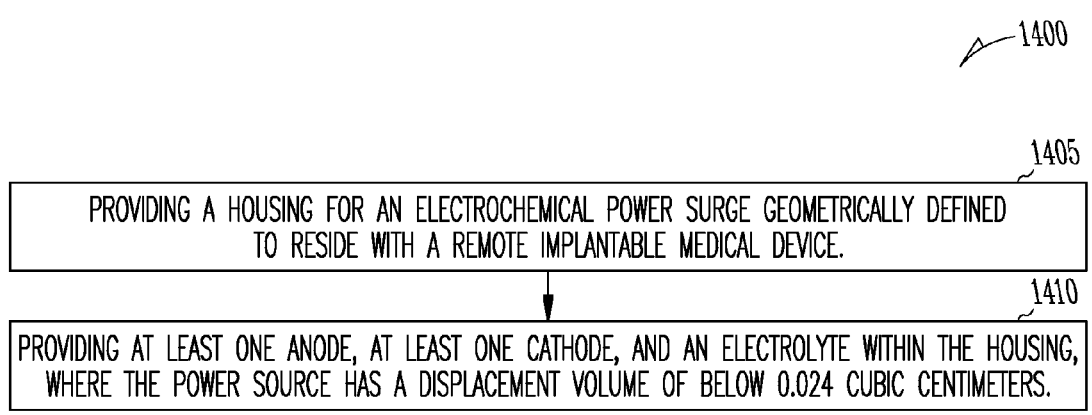
FIG. 14 illustrates a flow diagram of a method for manufacturing an electrochemical power source for use in a remote implantable medical device, according to one embodiment.

FIG. 14 illustrates a flow diagram of a method for manufacturing an electrochemical power source for use in an implantable medical device, according to one embodiment. According to various embodiments, the method 1400 includes providing a housing geometrically defined to reside with an implantable medical device, at 1405. The method also includes providing at least one anode, at least one cathode, and an electrolyte within the housing, at 1410. According to various embodiments, the power source has a displacement volume of below 0.024 cubic centimeters and is adapted to provide electrical current used to operate the device.

According to various embodiments, providing the cathode includes providing a cathode including compressed powder, dough and/or slurry. The cathode can be formed directly in the battery container or pressed or coated onto an electrically conductive material. In various embodiments, the cathode includes at least one metal oxide, metal sulphide, metal selenide, metal halide or metal oxyhalide compound or their corresponding lithiated forms. The cathode may include manganese, vanadium, silver, molybdenum, tungsten, cobalt, nickel, or chromium. The cathode may also include a main group compound such as carbon monofluoride or iodine. Other compositions of the cathode are within the scope of this disclosure.

In this method, providing the anode includes providing an anode including carbon or a metal, according to various embodiments. The anode may include metals such as lithium, sodium, potassium, rubidium, cesium, magnesium, calcium, strontium, barium, tin, zinc or silver. Other compositions of the anode are within the scope of this disclosure.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter.

Figure 15:
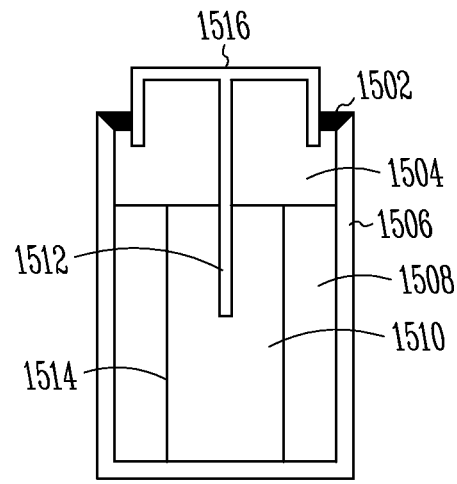
FIG. 15 shows a cross section of a bobbin battery, according to one embodiment of the present subject matter.

FIG. 15 shows a cross section of a bobbin battery, according to one embodiment of the present subject matter. Bobbin batteries benefit from having fewer inactive components and/or less of an inactive component. For example, some bobbin battery embodiments have less separator. Additionally, some bobbin battery embodiments have less current collector. While bobbin batteries can provide a reduced discharge rate over other battery configurations for a given size, they provide improved performance in applications which are less sensitive to discharge rate. The improved performance is due, in part, to the reduction in inactive materials, which can lead to reduced size.

A bobbin configuration includes a casing 1506. In various embodiments, the bobbin configuration includes an anode 1508. In various embodiments, the anode 1508 is electrically interconnected with the casing 1506. In various embodiments, the bobbin configuration includes a cathode 1510. The cathode 1510, in various embodiments, is connected to a terminal 1516 using a current collector 1512. Separator 1514 is disposed between the anode 1508 and the cathode 1510. The polarity of components discussed herein is selected to assist in explanation, and can be reversed without departing from the present scope of embodiments.

Various embodiments require sealing the internal components of the bobbin configuration. In some of these embodiments, a seal 1502 is disposed between the terminal 1516 and the casing 1506. In various embodiments, the seal 1502 resists electrical conductivity. In various embodiments, the seal 1502 additional provides mechanical structure to the bobbin configuration, orienting the terminal 1516 with respect to the casing 1506. Various embodiments include a space 1504 which is empty. Additional embodiments do not include space 1504. Some embodiments dispose a sealant in the space 1504. Additional embodiments dispose electrolyte in the space 1504.

Various embodiments incorporate battery chemistries compatible with bobbin style configurations. Embodiments within the present scope include, but are not limited to, at least one of a metal oxide, a metal sulfide, a metal selenide, a metal halide, a metal oxyhalide compound, and corresponding lithiated forms. Some of these embodiments include at least one of manganese, vanadium, silver, molybdenum, tungsten, cobalt, nickel, chromium, and main group compounds such as carbon monofluoride and iodine. Additionally, some embodiments include at least one of carbon, lithium, sodium, potassium, rubidium, cesium, magnesium, calcium, strontium, barium, tin, zinc or silver.

Primary battery chemistry embodiments fall within the present scope. Additionally, secondary battery chemistry embodiments fall within the present scope. In some embodiments a power source of an implantable medical device includes a plurality of batteries connected in series, parallel or a combination of series and parallel.

Various electrode constructions fall within the present scope. Embodiments compatible with bobbin construction are included, including monolithic electrodes, pelleted electrodes, and other electrodes which have a solid shape. Pelleted electrodes, in various embodiments, include pellets formed from compressed powder, dough or slurry. Some electrode embodiments are formed from a tightly wound ribbon which is wound unto itself without an insulator to separate progressive wraps from one another. Additionally, some embodiment include an electrode onto which is pressed or coated an electronically conductive material. Other electrode configuration embodiments compatible with bobbin batteries additionally fall within the present scope.

Additionally, various battery profiles using these electrodes fall within the present scope. Embodiments with the present scope include, but are not limited to, batteries having a cylindrical shape, batteries having a prismatic shape, batteries having a button shape, and batteries having other shapes. In some examples, batteries have shape which is determined as a function of the shape's impact on reducing blood flow. In some examples, batteries have shape which is determined as a function of the shape's impact on reducing tissue damage during implantation. As such, various embodiments include an annular anode. Some embodiments include an annular cathode. Embodiments discussed herein demonstrate an annular cathode concentric with an annular anode.

Figure 16:
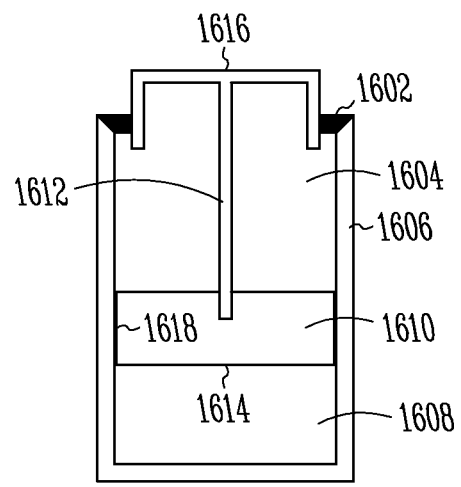
FIG. 16 shows a cross section of a bobbin battery, according to one embodiment of the present subject matter.

FIG. 16 shows a cross section of a bobbin battery, according to one embodiment of the present subject matter. In various embodiments, a bobbin configuration includes a casing 1606. In various embodiments, the bobbin configuration includes an anode 1608. In various embodiments, the anode 1608 is interconnected with the casing 1606. In various embodiments, the bobbin configuration includes a cathode

1610. The cathode 1610, in various embodiments, is connected to a terminal 1616 using a current collector 1612. In various embodiments, a separator 1614 is disposed between the anode 1608 and the cathode 1610. Additionally, in various embodiments, a separator 1618 is disposed between the cathode 1610 and the casing 1606. The polarity of components discussed herein is selected to assist in explanation, and can be reversed without departing from the present scope of embodiments.

Various embodiments require sealing the internal components of the bobbin configuration. In some of these embodiments, a seal 1602 is disposed between the terminal 1616 and the casing 1606. In various embodiments, the seal 1602 resists electrical conductivity. In various embodiments, the seal 1602 additional provides mechanical structure to the bobbin configuration, orienting the terminal 1616 with respect to the casing 1606. Various embodiments include a space 1604 which is empty. Additional embodiments do not include a space 1604. Some embodiments dispose a sealant in the space 1604. Additional embodiments dispose electrolyte in the space 1604.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus, comprising:
   an implantable electronics shell;
   electronics disposed in the implantable electronics shell;
   an implantable power source shell defining an implantable power source shell interior, the implantable power source shell being hermetically sealed to the implantable electronics shell with a first seal, with the electronics disposed outside the implantable power source shell;
   a power source disposed in the implantable power source shell interior, the power source being sealed in the implantable power source shell with a second seal, the power source comprising:
      an annular anode connected to a first terminal; and
      a cathode connected to a second terminal and disposed around the anode,
      wherein the anode and the cathode are arranged in a bobbin configuration,
   wherein an exterior of the apparatus includes an exterior of the implantable electronics shell and an exterior of the implantable power source shell.

2. The apparatus of claim 1, wherein the electronics shell and the power source shell are cylindrical.

3. The apparatus of claim 2, wherein the electronics shell and the power source shell are arranged in a column.

4. The apparatus of claim 1, wherein the implantable power source shell defines an implantable power source shell exterior shaped using modeled fluid dynamics and an implantable power source shell interior that approximately conforms to the power source shell exterior.

5. The apparatus of claim 4, wherein the power source defines a contoured power source exterior that approximately conforms to the implantable power source shell interior.

6. The apparatus of claim 1, wherein the implantable electronics shell defines an implantable electronics shell exterior shaped using modeled fluid dynamics.

7. The apparatus of claim 1, wherein an exterior of the apparatus has modeled fluid dynamics.

8. The apparatus of claim 7, wherein the implantable power source shell defines a contoured interior and an implantable power source shell exterior, wherein the anode and cathode are shaped to conform to the contoured interior of the implantable power source housing.

9. An apparatus, comprising:
   an implantable electronics shell;
   electronics disposed in the implantable electronics shell;
   an implantable power source shell defining an implantable power source shell interior, the implantable power source shell being hermetically sealed to the implantable electronics shell with a first seal, with the electronics disposed outside the implantable power source shell;
   a lead coupled to the electronics, the lead extending away from the implantable electronics shell to at least one electrode mounted distally on the lead;
   a power source disposed in the implantable power source shell interior, the power source being sealed in the implantable power source shell with a second seal, the power source comprising:
      an annular anode connected to a first terminal; and
      a cathode connected to a second terminal and disposed around the anode,
      wherein the anode and the cathode are arranged in a bobbin configuration,
   wherein an exterior of the apparatus includes an exterior of the implantable electronics shell and an exterior of the implantable power source shell.

10. The apparatus of claim 9, wherein the anode is monolithic.

11. The apparatus of claim 9, wherein the cathode includes a pellet of cathodic material, and the anode includes a pellet of anodic material.

12. The apparatus of claim 9, wherein the cathode is formed of a compressed material pressed into the implantable power source housing.

13. A method for construction an implantable device, comprising:
   forming an implantable electronics shell;
   disposing electronics in the implantable electronics shell;
   forming an implantable power source shell;
   forming a power source, comprising:
      forming an annular anode in the power source shell;
      disposing a separator inside the anode; and
      disposing a cathode inside the separator,
      wherein the anode and the cathode are arranged in a bobbin configuration;
   hermetically sealing the implantable electronics shell to the implantable power source shell, wherein the implantable power source shell forms a portion of an exterior of the implantable device.

14. The method of claim 13, wherein forming the implantable electronics shell comprises:
   modeling the exterior of the implantable electronics shell to provide reduced hydrodynamic drag in conditions measured at an implant site;
   modeling the exterior of the implantable electronics shell to provide reduced turbulence in conditions measured at the implant site;
   modeling the exterior of the implantable electronics shell to provide reduced fluid sheer stress in conditions measured at the implant site; and
   modeling the exterior of the implantable electronics shell to provide reduced stagnation in conditions measured at the implant site.

15. The method of claim 13, wherein forming the implantable power source shell comprises:

modeling the exterior of the implantable power source shell to provide reduced hydrodynamic drag in conditions measured at an implant site;

modeling the exterior of the implantable power source shell to provide reduced turbulence in conditions measured at the implant site;

modeling the exterior of the implantable power source shell to provide reduced fluid sheer stress in conditions measured at the implant site; and modeling the exterior of the implantable power source shell to provide reduced stagnation in conditions measured at the implant site.

16. The method of claim 13, wherein forming the anode includes forming the anode in an annular shape.

17. The method of claim 13, wherein forming the cathode includes forming the cathode in an annular shape.

18. The method of claim 13, wherein forming the cathode includes forming the cathode to be concentric with the anode.

19. The method of claim 13, wherein forming the anode includes forming the anode in a pellet shape.

20. The method of claim 13, wherein forming the cathode includes forming the cathode in a pellet shape.

* * * * *